(12) United States Patent
Yokoyama et al.

(10) Patent No.: US 6,548,447 B1
(45) Date of Patent: Apr. 15, 2003

(54) CATALYTIC OXIDATIVE DEHYDROGENATION PROCESS AND CATALYST

(75) Inventors: Chikafumi Yokoyama, Tokyo (JP); Sameer S. Bharadwaj, Minneapolis, MN (US); Lanny D. Schmidt, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/253,265

(22) Filed: Feb. 19, 1999

Related U.S. Application Data (62) Division of application No. 09/146,409, filed on Sep. 3, 1998, now Pat. No. 6,072,097, which is a continuation of application No. 08/720,562, filed on Sep. 30, 1996, now Pat. No. 5,905,180, which is a division of application No. 08/589,387, filed on Jan. 22, 1996, now abandoned.

(51) Int. Cl.⁷ ............................. B01J 23/62; B01J 23/89
(52) U.S. Cl. ..................... 502/331; 502/339; 502/345; 502/352
(58) Field of Search ................................. 502/331, 330, 502/339, 325, 326, 345, 352

(56) References Cited

U.S. PATENT DOCUMENTS

| | | |
|---|---|---|
| 3,562,797 A | 2/1971 | Hu |
| 3,617,518 A * | 11/1971 | Sinfelt et al. |
| 3,670,044 A | 6/1972 | Drehman et al. |
| 3,759,823 A * | 9/1973 | Davies et al. |
| 3,900,646 A | 8/1975 | Clyde |
| 3,957,685 A | 5/1976 | Heide et al. |
| 3,998,758 A | 12/1976 | Clyde |
| 4,053,556 A * | 10/1977 | Acres ......................... 423/239 |
| 4,078,743 A | 3/1978 | Kogan et al. |
| 4,080,394 A | 3/1978 | Antos |
| 4,087,259 A | 5/1978 | Fujitani et al. |
| 4,088,607 A | 5/1978 | Weidenbach et al. |
| 4,162,235 A * | 7/1979 | Acres et al. .................. 252/462 |
| 4,169,815 A | 10/1979 | Drehman |
| 4,189,405 A * | 2/1980 | Knapton et al. ............. 252/462 |
| 4,237,032 A * | 12/1980 | Evans et al. ................. 252/462 |
| 4,251,239 A | 2/1981 | Clyde et al. |
| 4,253,302 A | 3/1981 | Asano et al. |
| 4,308,233 A | 12/1981 | Narumiya et al. |
| 4,381,641 A * | 5/1983 | Madgavkar et al. ....... 60/39.06 |
| 4,384,986 A * | 5/1983 | Lecloux et al. |
| 4,440,874 A * | 4/1984 | Thompson .................. 502/327 |
| 4,568,595 A | 2/1986 | Morris |
| 4,652,687 A | 3/1987 | Imai et al. |
| 4,767,569 A | 8/1988 | Brophy et al. |
| 4,789,533 A * | 12/1988 | Baiker et al. |
| 4,795,818 A | 1/1989 | Becker et al. |
| 4,810,685 A | 3/1989 | Twigg et al. |
| 4,827,071 A | 5/1989 | Hazbun |
| 4,844,837 A | 7/1989 | Heck et al. |
| 4,863,707 A | 9/1989 | McShea, III et al. |
| 4,863,712 A | 9/1989 | Twigg et al. |
| 4,902,664 A * | 2/1990 | Wan ........................... 502/300 |
| 4,902,849 A | 2/1990 | McKay et al. |
| 4,927,857 A | 5/1990 | McShea, III et al. |
| 4,931,419 A | 6/1990 | Blanchard |
| 4,940,826 A | 7/1990 | Font Freide et al. |
| 5,023,276 A | 6/1991 | Yarrington et al. |
| 5,039,519 A | 8/1991 | Pinto |
| 5,073,657 A | 12/1991 | Warren |
| 5,105,052 A | 4/1992 | Font Freide et al. |
| 5,143,886 A | 9/1992 | Iezzi et al. |
| 5,152,976 A | 10/1992 | Fong et al. |
| 5,217,939 A | 6/1993 | Campbell |
| 5,219,816 A | 6/1993 | Zhou et al. |
| 5,258,567 A | 11/1993 | Kerby et al. |
| 5,264,200 A * | 11/1993 | Felthouse et al. ........... 423/522 |
| 5,278,123 A | 1/1994 | Chopin et al. |
| 5,306,684 A | 4/1994 | Itoh et al. |
| 5,374,410 A | 12/1994 | Grasselli et al. |
| 5,382,741 A | 1/1995 | Astbury et al. |
| 5,413,984 A | 5/1995 | Marecot et al. |
| 5,436,383 A | 7/1995 | Le Peltier et al. |
| 5,439,859 A | 8/1995 | Durante et al. |
| 5,516,741 A * | 5/1996 | Gascoyne et al. .......... 502/230 |
| 5,559,065 A * | 9/1996 | Lauth et al. |
| 5,593,935 A | 1/1997 | Golunski et al. |
| 5,625,111 A | 4/1997 | Astbury et al. |
| 5,639,929 A | 6/1997 | Bharadwaj et al. |

(List continued on next page.)

FOREIGN PATENT DOCUMENTS

| | | |
|---|---|---|
| CA | 2 004 219 | 5/1990 |
| CN | 1055303 A | 10/1991 |
| CN | 1069483 A | 3/1993 |
| CN | 1103010 A | 5/1995 |
| EP | 0 178 853 | 4/1986 |
| EP | 0 189 282 | 7/1986 |
| EP | 0 332 289 | 9/1989 |
| EP | 0 576 096 | 12/1993 |
| EP | 0 441 430 B1 | 3/1994 |
| EP | 0 638 534 A1 | 2/1995 |
| EP | 0 529 793 B1 | 5/1996 |
| WO | WO 90/06282 | 6/1990 |
| WO | WO 90/06297 | 6/1990 |

OTHER PUBLICATIONS

S. Bharadwaj et al., "Catalytic partial oxidation of alkanes on silver in fluidized bed and monolith reactors," *Applied Catalysis A: General,* 140, 73–97 (1996).

(List continued on next page.)

*Primary Examiner*—Tom Dunn
*Assistant Examiner*—Christina Ildebrando
(74) *Attorney, Agent, or Firm*—Mueting, Raasch & Gebhardt, P.A.

(57) ABSTRACT

A process for the production of a mono-olefin from a gaseous paraffinic hydrocarbon having at least two carbon atoms or mixtures thereof comprising reacting the hydrocarbons and molecular oxygen in the presence of a platinum catalyst. The catalyst consists essentially of platinum modified with Sn or Cu and supported on a ceramic monolith.

19 Claims, 6 Drawing Sheets

U.S. PATENT DOCUMENTS

| | | | |
|---|---|---|---|
| 5,648,582 A | | 7/1997 | Schmidt et al. |
| 5,654,491 A | | 8/1997 | Goetsch et al. |
| 5,658,497 A | | 8/1997 | Kumar et al. |
| 5,677,260 A | | 10/1997 | Dongara et al. |
| 5,714,092 A | | 2/1998 | van Looij et al. |
| 5,801,114 A | * | 9/1998 | Durand et al. ............... 502/302 |
| 6,040,266 A | * | 3/2000 | Fay, III et al. |

OTHER PUBLICATIONS

S. Bharadwaj et al., "Olefins by Catalytic Oxidation of Alkanes in Fluidized Bed Reactors," *Journal of Catalysis, 155*, 403–413 (1995).

S. Bharadwaj et al., "Synthesis Gas Formation by Catalytic Oxidation of Methane in Fluidized Bed Reactors," *Journal of Catalysis, 146*, 11–21 (1994).

S. Bharadwaj et al., "Catalytic partial oxidation of natural gas to syngas,"*Fuel Processing Technology, 42*, 109–127 (1995).

L. Schmidt et al., "Catalytic Partial Oxidation Reactions and Reactors," *Chemical Engineering Science, 49*(24A), 3981–3994 (1994).

F. Ragaini et al., "Homogeneous catalysis in water without charged ligands. Reduction of nitrobenzene to aniline by $CO/H_2O$ catalysed by $[Rh(CO)_4]-$," *Journal of Molecular Catalysis A: Chemical, 105*, 145–148 (1996).

C. Yokoyama et al., "Platinum–tin and platinum–copper catalysts for autothermal oxidative dehydrogenation of ethane to ethylene," *Catalysis Letters, 38*, 181–188 (1996).

DOE Grant No. DE–FG02–88ER13878–A02 (1991).

NSF Grant No. CTS–9311295 No date available.

A. T. Ashcroft, et al., "Partial oxidation of methane to synthesis gas using carbon dioxide," *Letters to Nature, 352*, 225–226 (1991).

R. Bacaud et al., "Mössbauer Spectra Investigation of the Role of Tin in Platinum—Tin Reforming Catalysts,"*Journal of Catalysis, 69*, 399–409 (1981).

T.P. Chojnacki et al., "Microstructures of Pt–Sn and Rh–Sn Particles on $SiO_2$," *Journal of Catalysis, 129*, 473–485 (1991).

V. R. Choudhary, "Energy efficient methane–to–syngas conversion with low $H_2/CO$ ratio by simultaneous catalytic reactions of methane with carbon dioxide and oxygen," *Catalysis Letters, 32*, 391–396 (1995).

F.M. Dautzenberg, "Conversion of n–Hexane over Monofunctional Supported and Unsupported PtSn Catalysts," *Journal of Catalysis, 63*, 119–128 (1980).

D. A. Hickman, et al., "Alternative Catalyst Supports for HCN Synthesis and $NH_3$ Oxidation," *Ind. Eng. CHem. Res., 32*(5), 809–817 (1993).

M. Huff et al., "Partial oxidation alkanes over noble metal coated monoliths," *Catalysts Today, 21*, 113–128 (1994).

M. Huff et al., "Ethylene Formation by Oxidative Dehydrogenation of Ethane over Monoliths at Very Short Contact Times," *J. Phys. Chem., 97*, 11815–11822 (1993).

J.–F. Le Page et al., *Applied Heterogeneous Catalysis,* pp. 90–91 (1987).

T. Matsuda et al., "Dehydrogenation of isobutane to isobutene in a palladium membrane reactor," *Applied CatalysisA: General, 96*, 3–13 (1993).

A.C. Muller, "Surface Study of Platinum–Tin Bimetallic Reforming Catalysts,"*Journal of Catalysts, 56*, 65–72 (1979).

E. Ruckenstein et al., "Role of Support in $CO_2$ Reforming of $CH_4$ to Syngas over Ni Catalysts," *Journal of Catalysis, 162*, 230–238 (1996).

P. M. Torniainen et al., "Comparison of Monolith–Supported Metals for the Direct Oxidation of Methane to Syngas," *Journal of Catalysis, 145*, 1–10 (1994).

H. Verbeek et al., "The Study of the Alloys of Platinum and Tin by Chemisorption," *The Journal of Catalysis, 42*, 257–267 (1976).

P.R. Gray et al., "A Mössbauer investigation of a platinum–tin paraffin oxidative dehydrogenation catalyst,"*Abstracts of Papers, 174 $^{th}$ ACS National Meeting,* Abstract No. COLL–48, Aug. 28, 1977–Sep. 2, 1977, Chicago, Il.

* cited by examiner

CATALYTIC OXIDATIVE DEHYDROGENATION PROCESS AND CATALYST

This is a division of application Ser. No. 09/146,409, filed Sep. 3, 1998, now U.S. Pat. No. 6,072,097, which in turn is a continuation of application Ser. No. 08/720,562, filed Sep. 30, 1996 now U.S. Pat. No. 5,905,180, which, in turn, is a division of application Ser. No. 08/589,387, filed Jan. 22, 1996, which has been abandoned, all of which are incorporated herein by reference.

This invention was made with government support under grant number CTS 9311295 awarded by the National Science Foundation. The government has certain rights in the invention.

BACKGROUND OF THE INVENTION

1. Field of the Invention

This invention relates to oxidation/dehydrogenation catalysts and a process for the dehydrogenation of dehydrogenatable hydrocarbons in the presence of the oxidation/dehydrogenation catalysts and an oxygen-containing gas.

The dehydrogenation of hydrocarbons is an important commercial process. This is because of the great demand for dehydrogenated hydrocarbons as feedstocks for industrial processes. For example, dehydrogenated hydrocarbons are utilized in the manufacture of various products such as detergents, high octane gasolines, and pharmaceutical products among others. Plastics and synthetic rubbers are other products which may be produced through use of dehydrogenated hydrocarbons. One example of a specific dehydrogenation process is dehydrogenating isobutane to produce isobutene which may be etherified to produce gasoline octane improvers, polymerized to provide adhesive tackifying agents, viscosity-index additives and plastic antioxidants.

2. Related Art

Various reticulated ceramic structures are described in the art: U.S. Pat. No. 4,251,239 discloses fluted filter of porous ceramic having increased surface area; U.S. Pat. No. 4,568,595 discloses reticulated ceramic foams with a surface having a ceramic sintered coating closing off the cells; U.S. Pat. No. 3,900,646 discloses ceramic foam with a nickel coating followed by platinum deposited in a vapor process; U.S. Pat. No. 3,957,685 discloses nickel or palladium coated on a negative image ceramic metal/ceramic or metal foam; U.S. Pat. No. 3,998,758 discloses ceramic foam with nickel, cobalt or copper deposited in two layers with the second layer reinforced with aluminum, magnesium or zinc; U.S. Pat. Nos. 4,810,685 and 4,863,712 disclose negative image reticulated foam coated with active material, such as, cobalt, nickel or molybdenum coating; U.S. Pat. No. 4,308,233 discloses a reticulated ceramic foam having an activated alumina coating and a noble metal coating useful as an exhaust gas catalyst; U.S. Pat. No. 4,253,302 discloses a foamed ceramic containing platinum/rhodium catalyst for exhaust gas catalyst; and U.S. Pat. No. 4,088,607 discloses a ceramic foam having an active aluminum oxide layer coated by a noble metal containing composition such as zinc oxide, platinum and palladium.

The supports employed in the present invention are generally of the type disclosed in U.S. Pat. No. 4,810,685 using the appropriate material for the matrix and are generally referred to in the art and herein as "monoliths".

The monoliths with various catalytic materials deposited thereon have also been employed for the production of synthesis gas (PCT WO 90/06279) and nitric acid (U.S. Pat. No. 5,217,939)

U.S. Pat. No. 4,940,826 (Freide, et al) discloses the oxidative dehydrogenation of gaseous paraffinic hydrocarbons having at least two carbon atoms or a mixture thereof by contacting the hydrocarbon with molecular oxygen containing gas over a supported platinum catalyst where the support is alumina such as gamma alumina spheres and monoliths such as cordierite or mullite. The desired products are the corresponding olefins.

Various modifiers are disclosed for the monolith/noble metal. Canadian patent 2,004,219 lists Group IV elements as coating materials for monoliths and U.S. Pat. No. 4,927,857 discloses a platinum/monolith partial oxidation catalyst supplemented with copper used in conjunction with a steam reforming process. Neither of these references suggests the use of modified platinum/monolith catalyst in oxidative dehydrogenations.

SUMMARY OF THE INVENTION

Briefly the present invention is a process for the production of a mono-olefin from a gaseous paraffinic hydrocarbon having at least two carbon atoms or mixtures thereof comprising reacting said hydrocarbons and molecular oxygen in the presence of a platinum catalyst modified with Sn or Cu, preferably in the substantial absence of Pd and Rh on a monolith support. The catalysts consist essentially of platinum modified with Sn or Cu on a ceramic monolith support, preferably alumina or zirconia monolith support.

DETAILED DESCRIPTION OF PREFERRED EMBODIMENTS

The composition of the ceramic support can be any oxide or combination of oxides that is stable at the high temperatures of operation, near 1000° C. The support material should have a low thermal expansion coefficient. The components of the oxide support should not phase separate at high temperatures since this may lead to loss of integrity. Components of the oxide support should not become volatile at the high reaction temperatures. Suitable oxide supports include the oxides of Al ($\alpha$-$Al_2O_3$), Zr, Ca, Mg, Hf, and Ti. Combinations of these can be produced to tailor the heat expansion coefficient to match the expansion coefficient of the reactor housing.

The structure and composition of the support material is of great importance. The support structure affects the flow patterns through the catalyst which in turn affects the transport to and from the catalyst surface and thus the effectiveness of the catalyst. The support structure should be In addition to Sn and Cu, several other metals were evaluated as modifiers. Pt/Ag exhibited comparable conversion and $C_2H_4$ selectivity to Pt alone. Experiments using Ag were identical to those described below but experiments were less extensive for poor catalysts (Pt/Mg, Pt/Ce, Pt/Ni, Pt/La, Pt/Co). The addition of the other metals lowered both conversion and olefin selectivity in the order of Sn>Cu>Pt alone>Ag>Mg>Ce>Ni>La>Co as demonstrated with ethane. With lower $C_2H_4$ selectivity, syngas (CO+$H_2$) formation became predominant. Pt/Au could not be ignited with $C_2H_6$+$O_2$. $NH_3$ and $O_2$ were used for light-off of the Pt/Au catalyst, however, the catalyst extinguished quickly when $C_2H_6$ was introduced in spite of the presence of $NH_3$. The results on the catalysts containing the various metals were summarized in Table I.

TABLE I

Comparison of Metals

| Catalyst | Atomic ratio (Metal:Pt) | Reaction temp ° C. | Conv. of $C_2H_6$ % | $S_{C_2H_4}$ % | $S_{COX}$ % | $Y_{C_2H_4}$ % | Max. $Y_{C_2H_4}$ (at $C_2H_6$:$O_2$) |
|---|---|---|---|---|---|---|---|
| Pt | 0 | 920 | 69.7 | 64.9 | 26.9 | 45.3 | 52.7 (1.5) |
| Pt/Sn | 1 | 912 | 71.5 | 68.2 | 24.1 | 48.8 | 55.3 (1.5) |
| Pt/Sn | 3 | 905 | 72.8 | 68.0 | 24.4 | 49.5 | 55.4 (1.5) |
| Pt/SN | 7 | 920 | 75.7 | 69.0 | 21.9 | 52.3 | 57.4 (1.7) |
| Pt/Cu | 1 | 928 | 74.4 | 68.1 | 23.8 | 50.7 | 55.0 (1.7) |
| Pt/Cu | 3 | extinguished in $C_2H_6$ + $O_2$ | | | | | |
| Pt/Ag | 1 | | 62.6 | 64.3 | 26.4 | 40.2 | 51.6 (1.7) |
| Pt/Mg | 3 | 943 | 65.1 | 60.6 | 33.6 | 39.5 | 43.4 (1.7) |
| Pt/Ce | 3 | 905 | 60.2 | 49.7 | 47.7 | 29.9 | 31.2 (1.7) |
| Pt/La | 3 | 905 | 56.0 | 41.7 | 56.0 | 23.4 | 24.8 (1.7) |
| Pt/Ni | 1 | 905 | 58.7 | 46.3 | 50.4 | 27.2 | 29.3 (1.7) |
| Pt/Co | 1 | 873 | 50.8 | 26.8 | 71.4 | 13.1 | 15.3 (1.7) |
| Pt/Au | 1 | extinguished in $C_2H_6$ + $O_2$ | | | | | |

Note. All conversions, selectivities, and temperatures at $C_2H_6$:$O_2$ = 1.9 and 5 slpm without preheat. Pt loadings of all catalysts are 2 wt %.

macroporous with 30 to 80 pores per linear inch. The pores should yield a tortuous path for the reactants and products such as is found in foam ceramics. Straight channel extruded ceramic or metal monoliths yield suitable flow dynamics only if the pore size is very small with >80 pores per linear inch.

The preferred catalyst of the present invention consists essentially of platinum modified with Sn or Cu (a mixture of Sn and Cu may be used) supported on a ceramic foam monolith, preferably on zirconia or $\alpha$-alumina. The platinum should be deposited on the surface of the ceramic to a loading of 0.2 to 90 wt. %, preferably 2 to 10 wt. %, and more preferably in the absence or substantial absence of palladium, rhodium, and gold. It has been found that palladium causes the catalyst to coke up and deactivate very quickly and thus should be excluded in any amount that is detrimental to the effectiveness of the catalyst Though rhodium does not lead to catalyst deactivation the product distribution is less favorable.

Preferably the Pt and modifying Sn or Cu is supported on an $\alpha$-alumina or zirconia ceramic foam monolith with 30 to 80 pores per linear inch, 50 to 90% void fraction, created in such a way to yield a tortuous path for reactants. The Pt and modifiers may be supported on a ceramic foam monolith comprised of any combination of $\alpha$-alumina, zirconia, titania, magnesia, calcium oxide, or halfnium oxide such that the support is stable up to 1100° C. and does not undergo detrimental phase separation that leads to loss in catalyst integrity.

The paraffins which are suitable for the present process are generally those that can be vaporized at temperatures in the range of 25 to 400° C. at pressures of 0.1 to 5 atm. These are generally $C_2$ to $C_{20}$ carbon atom alkanes either alone or in mixtures, preferably having two to eight carbon atoms. Suitable alkanes include ethane, propane, n-butane isobutane, n-pentane, isoamylenes, n-hexane, isohexanes, n-heptane, isoheptane, octane and isooctanes. Since a preferred embodiment includes a preheating of the feed to the reaction zone, the necessity to heat an alkane feed above ambient temperature to obtain a vaporous feed is not a negative consideration.

The feed may include both linear and branched alkanes. It has been observed in a fuel rich regime for the oxidative dehydrogenation of n-butane that the oxygen is completely consumed, whereas for the isobutane oxidations it is not. This oxygen breakthrough suggests a rate limiting step for isobutane. It is a proposed theory that the rates of these reactions should be related to the strengths of C—H bonds that must be broken. Thus, it may be desirable to preheat those feeds which are determined to have relatively strong C—H bonds to increase the rate of the initiation step. The feeds may be preheated to temperatures in the range of 0 to 500° C., preferably 25 to 400° C.

The present invention discloses the catalytic oxidative dehydrogenation of hydrocarbons. Mixtures of hydrocarbons and oxygen are flammable between given compositions. The feed compositions cited in this invention are outside the flammability limits for the cited hydrocarbons. In all cases, the feed compositions are on the fuel-rich side of the upper flammability limit. The compositions range from 2 to 16 times the stoichiometric fuel to oxygen ratios for combustion to $CO_2$ and $H_2O$. Some molar ratios are set out below in Table II.

TABLE II

| Fuel | Operable Fuel: oxygen molar ratio | Preferred Fuel: oxygen molar ratio |
|---|---|---|
| Ethane | 0.8–2.5 | 1.5–2.0 |
| Propane | 0.5–1.5 | 0.8–1.3 |
| n-Butane | 0.45–1.0 | 0.6–0.8 |
| i-Butane | 0.45–2.25 | 1.4–2.1 |

As the diluent is reduced and as the reactants are preheated, the flammability limits widen, but it is under these conditions that higher fuel to oxygen ratios (farther from the flammable range) are preferred. This preference is based on catalyst performance with the extra measure of safety an added benefit.

Under the conditions of the present process, olefin cracking, CO disproportionation and reverse steam reforming of carbon can occur, and may lead to coke formation. It has been found by varying the catalyst contact time, the amount of time allowed for these secondary reactions can be controlled. At higher flow rates the olefin products spend less time in contact with the catalyst and higher olefin selectivities and less coking are observed.

The present invention discloses the catalytic oxidative dehydrogenation of hydrocarbons in an autothermal reactor at millisecond contact time. High yields of mono-olefins are obtained with a catalyst contact time ranging from 0.1 to 20 milliseconds when using a ceramic foam monolith of 50 to 90% porosity and 0.2 to 1 cm in depth. Under operating conditions, this corresponds to GHSV of 60,000 to 3,000,000 $hr^{-1}$.

The flow rates are in the range of 60,000–10,000,000 $hr^{-1}$ GHSV, preferably in the range of 300,000 up to 3,000,000 $hr^{-1}$ GHSV may be used.

Under the conditions of the present process it can be determined that several reactions may occur namely (1) complete combustion (strongly exothermic); (2) partial oxidation to syngas (exothermic); (3) oxidative dehydrogenation (exothermic); (4) dehydrogenation (endothermic) and cracking (endothermic).

The overall process can be carried out autothermally. The heat produced by exothermic reactions provides the heat for endothermic reactions. The process does not require the addition of heat.

However, improved results are obtained when moderate amounts of heat are supplied to the system. Preheating the feed shifts the product distribution from the more exothermic reactions (combustion and partial oxidation) to the less exothermic (oxidative dehydrogenation) and endothermic (dehydrogenation and cracking) reactions. Since oxygen is the limiting reactant, this shift improves the process conversion. The selectivity is improved since the less exothermic and endothermic reactions are the desired reactions.

EXAMPLES

The reactor used in the following examples consisted of a quartz tube with an inside diameter of 18 mm containing the catalytic monolith which was sealed into the tube with high temperature alumina-silica cloth that prevented bypass of the reactant gases around the edges of the catalyst. To reduce radiation heat loss and better approximate adiabatic operation, the catalyst was immediately preceded and followed by inert alumina extruded monolith heat shields. The outside of the tube near the reaction zone was insulated.

The Pt/M (M=Sn, Cu, Ag, Mg, Ce, La, Ni, Co, and Au) bimetallic catalysts were prepared as follows: First, Pt was added to $\alpha$-$Al_2O_3$ foam monoliths (17 mm diameter×10 mm long, 45 pores per inch (ppi) by impregnation with aqueous solutions of $H_2PtCl_6$. The samples were dried in vacuum at room temperature, followed by calcination at 100° C. for 0.5 hr. and at 350° for 2 hrs. in oxygen. The second metal was then added by impregnation with aqueous solutions of corresponding metal salts: $SnCl_2$, $Cu(NO_3)_2$, $AgNO_3$, $Mg(NO_3)_2$, $Ce(NO_3)_3$, $La(NO_3)_3$, $Ni(OOCCH_3)_2$, $Co(OOCCH_3)_2$, and $AuCl_3$. The Pt/M monoliths were then dried in vacuum at room temperature, calcined at 100° C. for 0.5 hr and at 700° C. for 1.5 hrs. in oxygen, and then reduced at 700° C. for 1.5 hr. in hydrogen. Pt loadings of all samples were either 2 or 5 wt %. The other metal loadings are summarized in Table 1.

The catalysts are prepared by depositing Pt, a mixture of components or components sequentially on commercially available ceramic foam monoliths. The foam monoliths, available from Hi-Tech Ceramics, Inc., are composed of either $\alpha$-$Al_2O_3$ or $ZrO_2$ with 30, 45 or 80 pores per linear inch (ppi). It is important to note that these catalysts are not microporous. The monoliths are not wash-coated and are estimated to have a surface area of less than 70 $m^2/g$. Suitable catalysts contain 0.2 to 20 wt % Pt and tin in an atomic ratio to Pt of 0.5 to 7:1 or copper in an atomic ratio to Pt of 0.5 to <3:1.

Gas flow into the reactor was controlled by mass flow controllers which had an accuracy of ±0.1 slpm for all gases. The feed flow rates ranged from 5 slpm total flow, corresponding to 37 cm/s superficial velocity (i.e. the velocity of the feed gases upstream from the catalyst, approximately 250 cm/s in the monolith at reaction conditions) at room temperature and atmospheric pressure. For ethane oxidation the ethane:oxygen ratio was varied from 1.5 to 2.1 at a fixed nitrogen dilution (30%). For butane oxidation, the butane::oxygen ratio was changed from 0.8 to 1.4 at 50% nitrogen. In all runs, the reactor pressure was maintained at 1.4 atm. The runs were carried out with $O_2$ as the oxidant. $N_2$ was typically added at a percent of the feed as an internal GC calibration standard. The reaction temperature was ≈1000° C. and contact times were from 0.2 to 40 msec. Product gases were fed through heated stainless steel lines to an automated gas chromatograph. Shutdown of the reactor was accomplished by turning off oxygen before alkane.

The product gases were analyzed by a gas chromatograph equipped with a single Hayesep DB packed column. For quantitative determination of concentrations, standards were used for all species except for $H_2O$, which was obtained most reliably from an oxygen atom balance. Nitrogen was used as an internal GC calibration standard. The selectivity data shown was calculated on a carbon atom or a hydrogen atom basis, as described below.

To convert the product gas concentrations to molar quantities for a given feed basis, the mole number change due to the chemical reactions was calculated using the measured $N_2$ concentration. Since $N_2$ is an inert in this system, the ratio of product gas to feed gas moles was inversely proportional to the ratio of product gas $N_2$ concentration to feed gas $N_2$ concentration. Individual species concentrations were measured with a reproducibility estimated to be ±2%.

Temperatures were monitored using thermocouples inserted from the rear of the quartz tube in one of the center channels of the inert monolith immediately after the catalytic monolith. The reactor was operated at a steady state temperature which is a function of the heat generated by the exothermic and endothermic reactions and the heat losses from the reactor.

Although the process in steady state is autothermal with feed gases at room temperature, heat was supplied initially to ignite the reaction. A mixture of hydrocarbon and air near the stoichiometric composition for production of synthesis gas was fed to the reactor, and the reactants were heated to the heterogeneous ignition temperature ($\approx 230°$ C. for $C_2$ to $C_4$ hydrocarbons). After light-off, the external heat source was removed (unless feed preheating is indicated), the reaction parameters were adjusted to the desired conditions, and steady state was established ($\approx 10$ min) before analysis. For situations where the catalyst was not ignited with a mixture of alkane and oxygen, e.g. Ag as a modifier, a $NH_3/O_2$ was used for light-off and $NH_3$ was then gradually exchanged for the alkane. Data shown were reproducible for time periods of at least several hours and on several catalyst samples.

For $C_2H_6$ oxidation, the major products over all catalysts were $C_2H_4$, CO, $CO_2$, $CH_4$, $H_2$, and $H_2O$. Traces of $C_2H_2$, $C_3H_6$, $C_3H_8$, and $C_4H_8$ were observed, usually with selectivities <2%. The conversions of oxygen were always above 97%, so reactions always go to completion.

EXAMPLE 1

Ethane

Pt, Pt/Sn and Pt/Cu Catalysts

Figure 1:
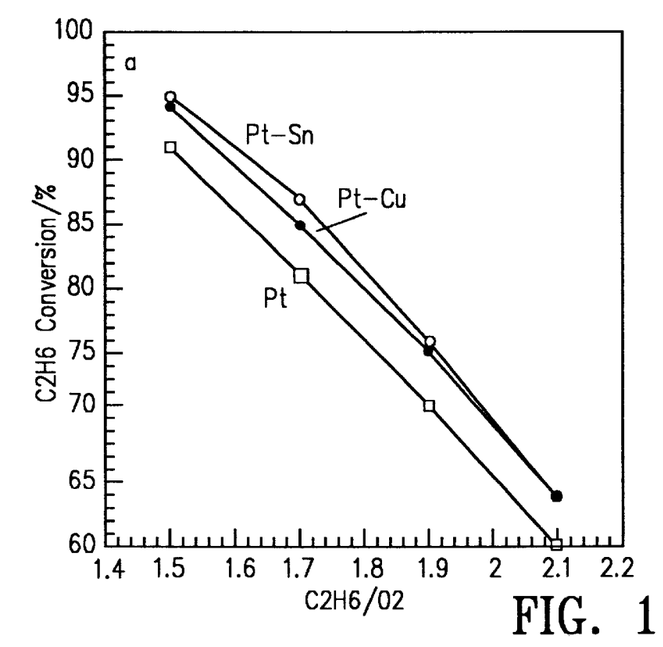
FIG. 1 shows ethane conversion as a function of the ethane:oxygen ratio for Sn and Cu modified Pt monolith catalyst compared to Pt alone.
Figure 2:
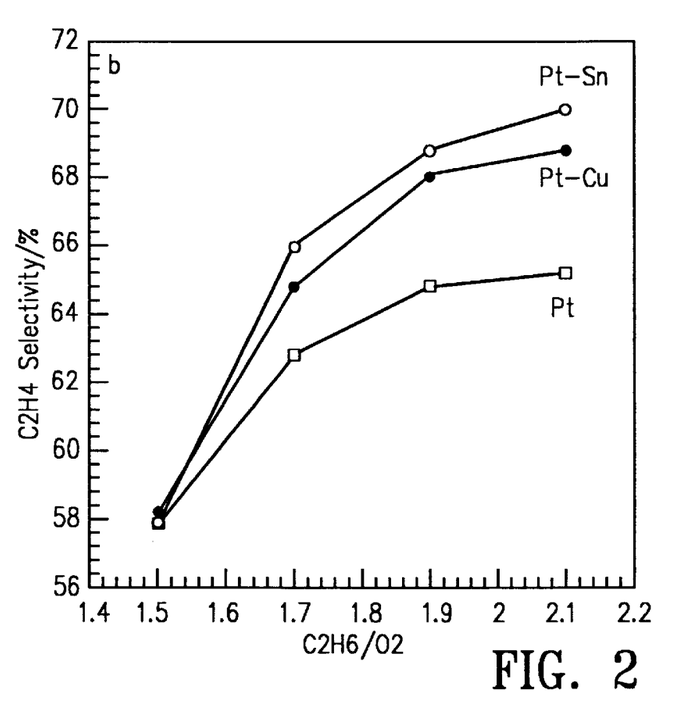
FIG. 2 shows ethylene selectivity as a function of the ethane:oxygen ratio for Sn and Cu modified Pt monolith catalyst compared to Pt alone.
Figure 3:
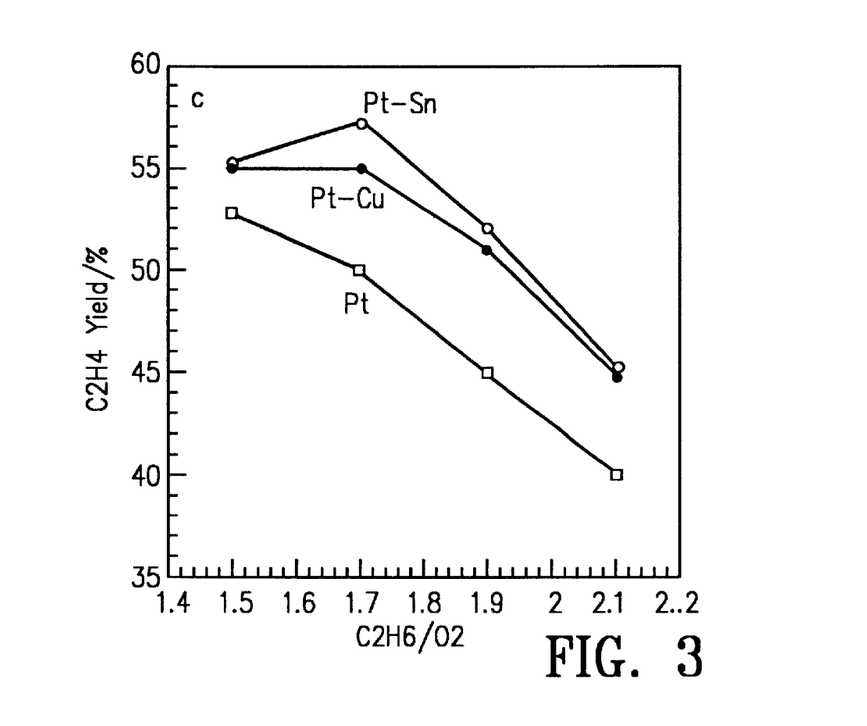
FIG. 3 shows ethylene yield as a function of the ethane:oxygen ratio for Sn and Cu modified Pt monolith catalyst compared to Pt alone.
Figure 4:
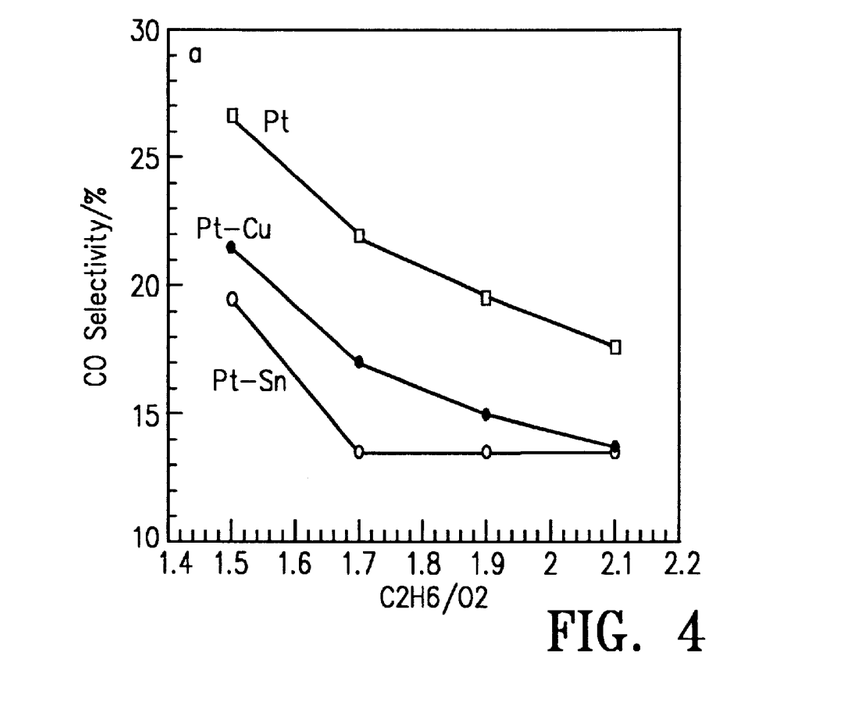
FIG. 4 shows CO selectivity as a function of the ethane:oxygen ratio for Sn and Cu modified Pt monolith catalyst compared to Pt alone.
Figure 5:
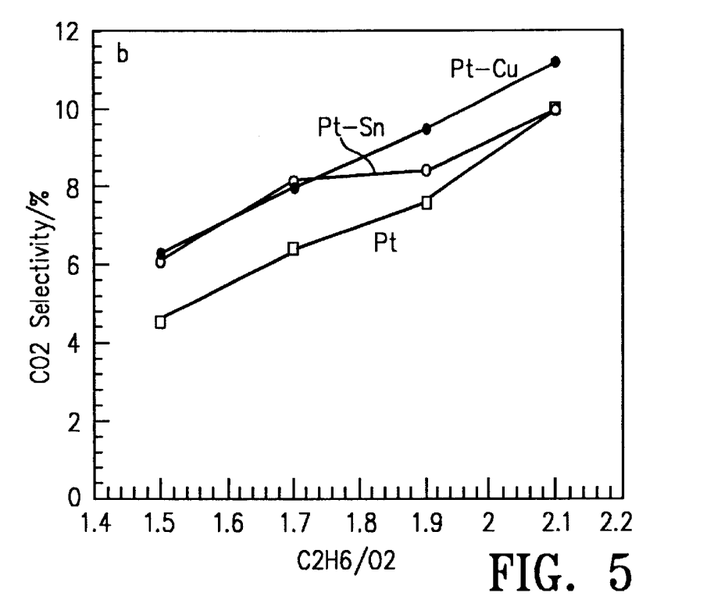
FIG. 5 shows $CO_2$ selectivity as a function of the ethane:oxygen ratio for Sn and Cu modified Pt monolith catalyst compared to Pt alone.
Figure 6:
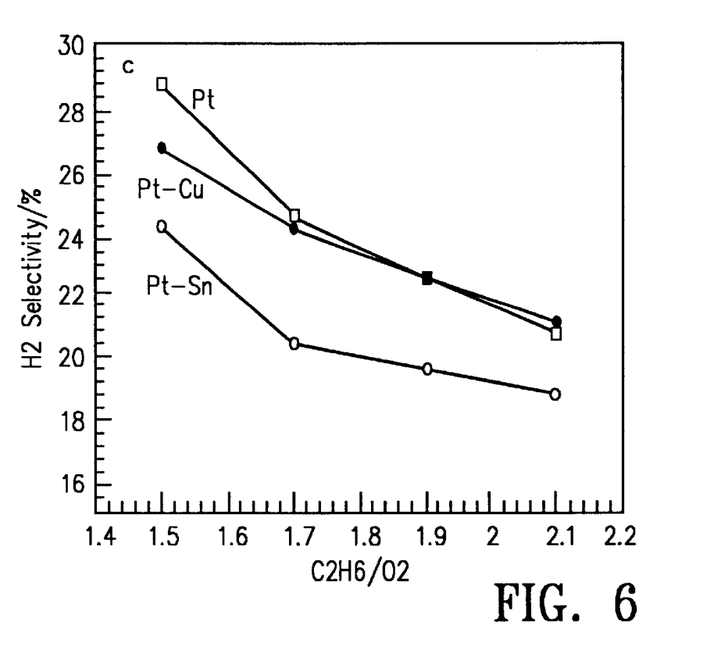
FIG. 6 shows $H_2$ selectivity as a function of the ethane:oxygen ratio for Sn and Cu modified Pt monolith catalyst compared to Pt alone.
Figure 7:
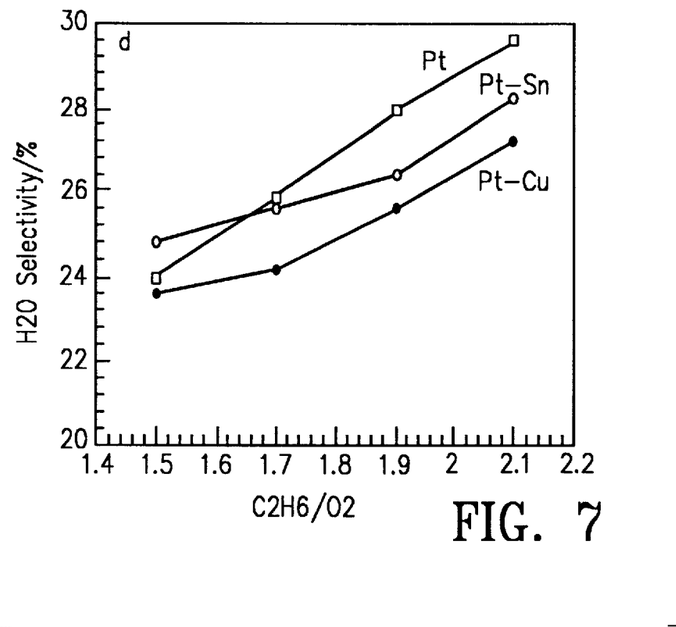
FIG. 7 shows $H_2O$ selectivity as a function of the ethane:oxygen ratio for Sn and Cu modified Pt monolith catalyst compared to Pt alone.

FIGS. 1, 2, and 3 show the $C_2H_6$ conversion, $C_2H_4$ selectivity, and $C_2H_4$ yield for oxidative dehydrogenation of ethane over Pt, Pt/Sn (Sn:Pt=7:1), and Pt/Cu (Cu:Pt=1:1) as a function of the feed composition (2.0 is the ethylene stoichiometric ratio). With increasing feed composition, the conversion decreased while the selectivity increased over the three catalysts. The addition of Sn significantly enhanced both the conversion (by $\approx 7\%$) and the selectivity (by $\approx 5\%$), which produced the highest $C_2H_4$ yield of 57% at 25° C. feed in this study. The Pt/Cu also showed higher conversion and higher selectivity than Pt, the maximum yield being 55%. As shown in FIGS. 4, 5, 6 and 7, both Pt/Sn and Pt/Cu showed 5≈9% lower CO selectivity and 1≈2% higher $CO_2$ selectivity than Pt. Among minor products, more $C_2H_2$ and $C_4H_8$ were formed on both Pt/Sn and Pt/Cu than on Pt. The addition of Sn or Cu inhibited CO production and promoted the formation of olefins and acetylene without significant change in $CH_4$ selectivities.

The reaction temperatures decreased from 1000 to 900° C. as the $C_2H_6:O_2$ ratio increased from 1.5 to 2.1 and temperatures were same to within ±20° C. on these three catalysts.

No deactivation or volatilization of the catalysts were observed for several hours. No significant coke formation on the catalysts was observed.

EXAMPLE 2

Ethane

Loadings of Pt, Sn, and Cu

Figure 8:
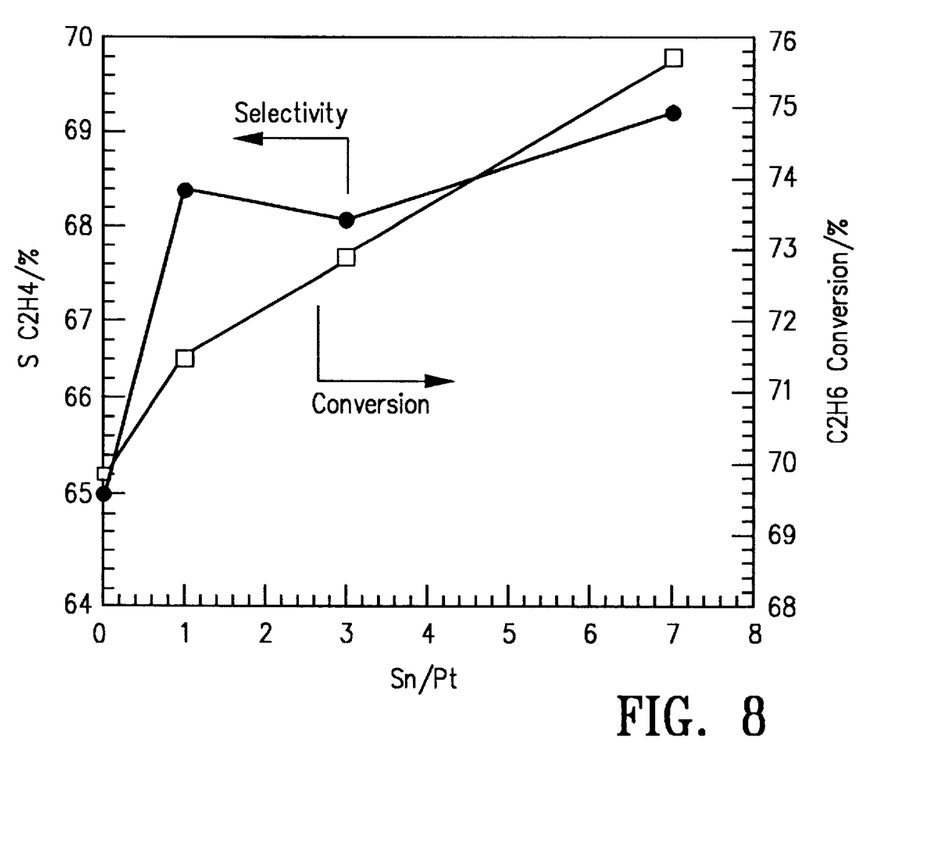
FIG. 8 plots the conversion of ethane and ethylene selectivity as a function of the ratio of Sn:Pt.

FIG. 8 shows plots of $C_2H_6$ conversion and $C_2H_4$ selectivity as functions of Sn:Pt ratio at a feed near the oxidative dehydrogenation stoichiometry ($C_2H_6:O_2=1.9$). The conversion increased with increased Sn:Pt ratio. On the other hand, the addition of a small amount of Sn (Sn:Pt=1:1) enhanced the selectivity significantly and the further addition led to a slight increase in the selectivity.

Pt/Cu (Cu:Pt=1:1) showed comparable results to Pt:Sn, as described above. However, Pt/Cu (Cu:Pt=3:1) could not be ignited in the mixture of $C_2H_6$ and $O_2$. A $NH_3:O_2$ mixture was used for ignition, but the catalyst extinguished upon exchange of $NH_3$ for $C_2H_6$, A sample of 5 wt % Pt was nearly identical to 2 wt % Pt, although the $C_2H_6$ conversion was 1% lower with 5 wt % loading. The addition of Sn to 5 wt % Pt also enhanced both the conversion and $C_2H_4$ selectivity. The 5 wt % Pt/Sn (Sn:Pt=1:1) exhibited comparable results (1% higher conversion and 1% lower selectivity to 2 wt % Pt/Sn (Sn:Pt=1:1). This fact confirms that Sn acts as a promoter for ethane oxidation, regardless of Pt loadings. Neither 5 wt % Pt/Cu (Cu:Pt=1:1) the 2 wt % Pt/Cu (Cu:Pt=3:1) worked autothermally.

EXAMPLE 3

Preheat

Figure 9:
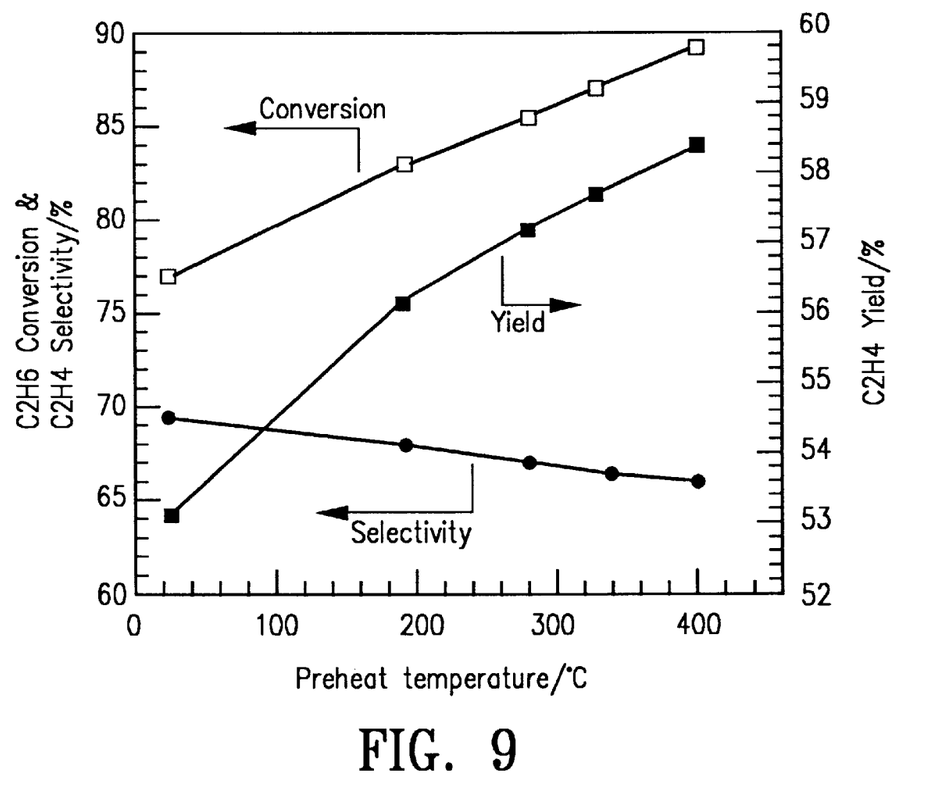
FIG. 9 illustrates the effect of feed preheating on ethane conversion, ethylene selectivity and ethylene yield.

FIG. 9 shows the effect of preheat on the conversion, selectivity, and yield over Pt/Sn (7:1) catalyst at $C_2H_6:O_2=1.9$. Preheat of reaction gases up to 400° C. increased the conversion from 77 to 89% and decreased the selectivity from 69 to 65%, which led to an increase in yield from 53 to 58%.

EXAMPLE 4 n-Butane

Figure 10:
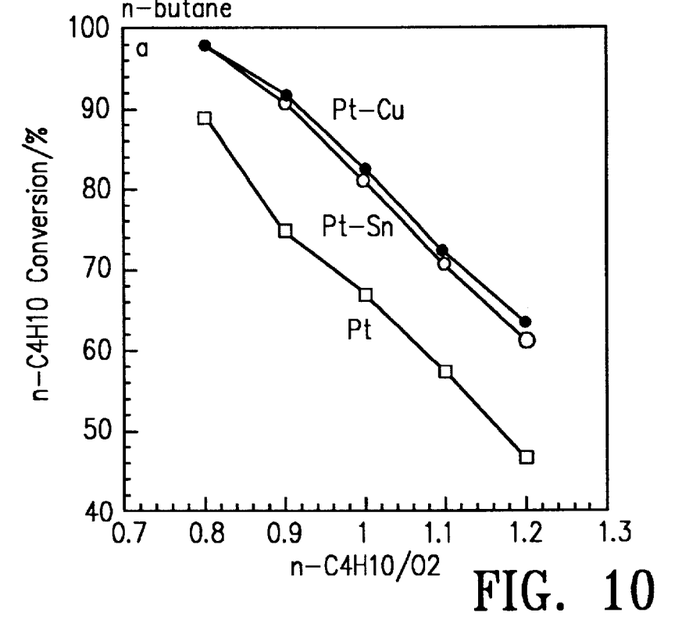
FIG. 10 shows n-butane conversion as a function of the butane:oxygen ratio for Sn and Cu modified Pt monolith.

Oxidative dehydrogenation of n-butane was examined over Pt, Pt/Sn (Sn:Pt=3), and Pt/Cu Cu:Pt=1). Both Pt/Sn and Pt/Cu showed much higher $C_4H_{10}$ conversion (by $\approx 16\%$) than Pt as a function of feed composition (FIG. 10). On the three catalysts, the selectivities to $C_2H_4$ and $CO_X$ decreased and selectivity to $C_3H_6$ increased with increasing $C_4H_{10}:O_2$ ratio. The $C_4H_8$ selectivity was only 3–5% and increased slightly with increasing $C_4H_{10}:O_2$ ratio. The $C_2H_4$ selectivity from n-$C_4H_{10}$ was much higher on Pt/Sn and Pt/Cu than on Pt, while the $C_3H_6$ selectivity was much lower on Pt/Sn and Pt/Cu than on Pt.

EXAMPLE 5 i-Butane

Figure 11:
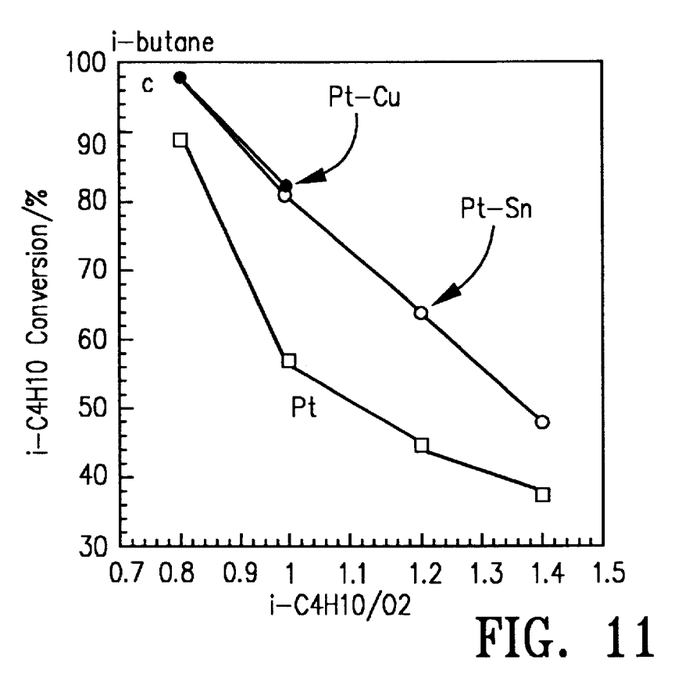
FIG. 11 shows i-butane conversion as a function of the i-butane:oxygen ratio for Sn and Cu modified Pt monolith catalyst compared to Pt alone.

Oxidation of i-butane was similar to n-butane. Both Pt/Sn (Sn:Pt=3) and Pt/Cu (Cu:Pt=1) showed much higher conversion (by 15–25%) than Pt (FIG. 11). With i-$C_4H_{10}$ the dominant olefins are i-$C_4H_8$ ($\approx 30\%$) and $C_3H_6$ ($\approx 30\%$). On all three catalysts, selectivities to $C_2H_4$ decreased and selectivities to $C_3H_6$ and i-$C_4H_8$ increased with increasing $C_4H_{10}:O_2$ ratio. As a function of conversion, Pt/Sn and Pt/Cu exhibited higher selectivities to olefins and acetylene than Pt at high conversion.

XRD

X-ray diffraction patterns were determined for Pt and Pt/Sn (Sn:Pt=1:1 and 7:1) catalysts after reaction. On Pt catalyst, only peaks of Pt metal were observed except for that of the $\alpha$-$Al_2O_3$ support. On the other hand, only PtSn and $Pt_3Sn$ peaks were observed for Pt/Sn catalysts and there were no Pt metal peaks. The PtSn:$Pt_3Sn$ ratio was higher for Pt:Sn (1:7) than for Pt:Sn (1:1). These results clearly indicate that Pt exists in the forms of only $Pt_3Sn$ and PtSn alloys on support for Pt/Sn catalyst.

The addition of Sn or Cu to Pt-monolith enhanced alkane conversion and olefin selectivities and suppressed $CO_x$ formation for the oxidative dehydrogenation reactions. Since Pt exists in the forms of only PtSn and $Pt_3Sn$ alloys on Pt/Sn catalyst, it is speculated that PtSn and $Pt_3Sn$ alloys are the active sites and are more selective to $C_2H_4$ formation that Pt.

The invention claimed is:

1. A catalyst composition consisting essentially of platinum modified with a mixture of metallic copper and metallic tin deposited on a support.

2. The catalyst composition according to claim 1 wherein the platinum is alloyed with metallic copper.

3. The catalyst composition according to claim 1 wherein the support comprises a monolith.

4. The catalyst composition according to claim 3 wherein the monolith comprises oxides of Al, Zr, Ca, Mg, Hf, Ti, or mixtures thereof.

5. The catalyst composition according to claim 1 wherein the catalyst was prepared by codepositing Pt with a mixture of metallic Cu and metallic Sn on the support.

6. The catalyst composition according to claim 1 wherein the catalyst was prepared by sequentially depositing Pt with a mixture of metallic Cu and metallic Sn on the support.

7. The catalyst composition according to claim 1 wherein the support has a surface area of less than 70 $m^2/g$ and has 30 to 80 pores per linear inch.

8. The catalyst composition according to claim 1 consisting essentially of Pt modified with metallic Cu and metallic Sn deposited over a zirconia monolith having 30 to 80 pores per linear inch and less than 70 $m^2/g$ surface area.

9. The catalyst composition according to claim 1 consisting essentially of Pt modified with metallic Cu and metallic Sn deposited over an alumina monolith having 30 to 80 pores per linear inch and less than 70 $m^2/g$ surface area.

10. The catalyst composition according to claim 1 wherein the support is a ceramic foam monolith.

11. The catalyst composition according to claim 1 wherein platinum is present in an amount of 0.2 wt % to 10 wt %, based on the total weight of the support and platinum catalyst.

12. A catalyst composition consisting essentially of platinum modified with a mixture of copper and tin deposited on a support, wherein the platinum is alloyed with copper and tin.

13. A catalyst composition consisting essentially of platinum modified with metallic copper or a mixture of metallic copper and metallic tin deposited on a alumina monolith support.

14. The catalyst composition of claim 13, wherein the support is a foam monolith.

15. A catalyst composition consisting essentially of platinum modified with metallic copper deposited on a monolith support, wherein the catalyst was prepared by sequentially depositing Pt with metallic Cu on the monolith support, and further wherein the support comprises alumina.

16. The catalyst composition according to claim 15 wherein the monolith further comprises oxides of Al, Zr, Ca, Mg, Hf, Ti, or mixtures thereof.

17. The catalyst composition according to claim 15 wherein the support has a surface area of less than 70 $m^2/g$ and has 30 to 80 pores per linear inch.

18. The catalyst composition according to claim 15 wherein the support is a ceramic foam monolith.

19. The catalyst composition according to claim 15 wherein platinum is present in an amount of 0.2 wt % to 10 wt %, based on the total weight of the support and platinum catalyst.

* * * * *